United States Patent
O'Neill et al.

[11] Patent Number: 5,807,326
[45] Date of Patent: Sep. 15, 1998

[54] RETROGRADE CORONARY SINUS CATHETER

[75] Inventors: William G. O'Neill, Ann Arbor, Mich.; Christopher M. Boykin, Athens, Tex.; Nelson L. Huldin, Pittsfield Township, Mich.; Sheila J. Hanson, Mequon, Wis.; Walter L. Carpenter, McHenry, Ill.; Thomas T. Vaalburg, Ann Arbor, Mich.

[73] Assignee: Minnesota Mining and Manufacturing Company, St. Paul, Minn.

[21] Appl. No.: 398,429

[22] Filed: Mar. 6, 1995

Related U.S. Application Data

[63] Continuation of Ser. No. 21,526, Feb. 23, 1993, Pat. No. 5,395,331, which is a continuation-in-part of Ser. No. 874,589, Apr. 27, 1992, Pat. No. 5,324,260.

[51] Int. Cl.⁶ .................................................. A61M 29/00
[52] U.S. Cl. ............................................. 604/96; 606/194
[58] Field of Search .......................... 604/96–101, 103; 606/191, 192, 194

[56] References Cited

U.S. PATENT DOCUMENTS

| | | | |
|---|---|---|---|
| D. 335,705 | 5/1993 | Buckberg et al. | D24/112 |
| D. 343,900 | 2/1994 | DeVries | D24/133 |
| D. 350,605 | 9/1994 | Williams | D24/133 |
| 735,400 | 8/1903 | McCully . | |
| 1,049,087 | 12/1912 | Hill . | |
| 1,190,179 | 4/1916 | Livingston . | |
| 1,289,106 | 12/1918 | Bullock . | |
| 2,308,484 | 1/1943 | Auzin et al. | 18/58 |
| 2,393,003 | 1/1946 | Smith | 128/349 |
| 2,701,559 | 2/1955 | Cooper | 128/2 |
| 2,927,584 | 3/1960 | Wallace | 128/349 |
| 2,983,512 | 5/1961 | Fleischer | 273/72 |
| 3,344,791 | 10/1967 | Foderick | 128/349 |
| 3,385,300 | 5/1968 | Holter | 128/348 |
| 3,521,620 | 7/1970 | Cook | 128/2.05 |
| 3,635,223 | 1/1972 | Klieman | 128/348 |
| 3,726,269 | 4/1973 | Webster, Jr. | 128/2.05 |
| 3,802,440 | 4/1974 | Salem et al. | 128/351 |

(List continued on next page.)

FOREIGN PATENT DOCUMENTS

| | | | |
|---|---|---|---|
| 0 141 006 | 5/1985 | European Pat. Off. | A61M 25/00 |
| 0 204 218 | 12/1986 | European Pat. Off. | A61M 25/00 |
| 0 231 601 | 8/1987 | European Pat. Off. | A61M 29/00 |
| 0 249 338 | 12/1987 | European Pat. Off. | A61M 25/00 |
| 0 280 225 | 8/1988 | European Pat. Off. | A61M 25/00 |
| 0 299 622 | 1/1989 | European Pat. Off. | A61M 25/00 |
| 0 303 757 | 2/1989 | European Pat. Off. | A61M 25/00 |
| 0 416 662 | 3/1991 | European Pat. Off. | A61M 25/04 |
| 0 620 022 | 10/1994 | European Pat. Off. | A61M 25/01 |
| 2 607 706 | 6/1988 | France | A61M 5/14 |
| 33 26 648 | 2/1985 | Germany | A61M 29/00 |
| WO 89/10155 | 11/1989 | WIPO | A61M 25/00 |
| WO 92/08510 | 5/1992 | WIPO | A61M 25/00 |
| WO 95/32756 | 12/1995 | WIPO | A61M 25/04 |

OTHER PUBLICATIONS

"Retroplegia® with Textured Ballon"; Research Medical, Inc., dated 1992.

Farcot et al.; "New Catheter–Pump System for Diastolic Synchronized Coronary Sinus Retroperfuson"; Medical Progress Through Technology; pp. 29–37 (1980).

Brochure entitled "Coronary Perfusion/Cardioplegia Infusion Cannulae" of Polystan A/S, Copenhagen, Denmark (undated).

(List continued on next page.)

*Primary Examiner*—Corrine M. McDermott
*Attorney, Agent, or Firm*—Gary L. Griswold; Robert W. Sprague; Stephen W. Bauer

[57] ABSTRACT

A coronary sinus catheter assembly for the retrograde infusion of cardioplegia solutions into the coronary sinus. The assembly comprises a catheter having a balloon with a plurality of segmented annular ribs, and a stylet having a relatively stiff proximal sleeve and a relatively flexible malleable wire extending distally from the sleeve.

45 Claims, 7 Drawing Sheets

U.S. PATENT DOCUMENTS

| | | | |
|---|---|---|---|
| 3,813,729 | 6/1974 | Szabo et al. | 16/119 |
| 3,815,608 | 6/1974 | Spinosa et al. | 128/349 |
| 3,854,473 | 12/1974 | Matsuo | 128/8 |
| 3,867,945 | 2/1975 | Long | 128/349 |
| 3,957,055 | 5/1976 | Linder et al. | 128/351 |
| 3,970,090 | 7/1976 | Loiacono | 128/349 |
| 4,215,703 | 8/1980 | Willson | 128/772 |
| 4,273,131 | 6/1981 | Olsen | 128/341 |
| 4,351,341 | 9/1982 | Goldberg et al. | 128/348 |
| 4,456,017 | 6/1984 | Miles | 128/772 |
| 4,465,072 | 8/1984 | Taheri | 128/348.1 |
| 4,529,400 | 7/1985 | Scholten | 604/95 |
| 4,531,936 | 7/1985 | Gordon | 604/49 |
| 4,545,390 | 10/1985 | Leary | 128/772 |
| 4,552,558 | 11/1985 | Muto | 604/100 |
| 4,619,274 | 10/1986 | Morrison | 128/772 |
| 4,632,668 | 12/1986 | Wilson, Jr. et al. | 604/8 |
| 4,648,384 | 3/1987 | Schmukler | 128/1 |
| 4,676,249 | 6/1987 | Arenas et al. | 128/657 |
| 4,682,607 | 7/1987 | Vaillancourt et al. | 128/772 |
| 4,689,041 | 8/1987 | Corday et al. | 604/53 |
| 4,713,049 | 12/1987 | Carter | 604/8 |
| 4,721,109 | 1/1988 | Healey | 128/334 |
| 4,753,637 | 6/1988 | Horneffer | 604/53 |
| 4,762,130 | 8/1988 | Fogarty et al. | 128/348.1 |
| 4,782,834 | 11/1988 | Maguire et al. | 128/344 |
| 4,834,709 | 5/1989 | Banning et al. | 604/170 |
| 4,846,186 | 7/1989 | Box et al. | 128/657 |
| 4,850,969 | 7/1989 | Jackson | 604/96 |
| 4,863,430 | 9/1989 | Klyce et al. | 604/164 |
| 4,886,067 | 12/1989 | Palermo | 128/657 |
| 4,898,168 | 2/1990 | Yule | 128/207 |
| 4,925,445 | 5/1990 | Sakamoto et al. | 604/96 |
| 4,927,412 | 5/1990 | Menasche | 604/96 |
| 4,931,330 | 6/1990 | Stier et al. | 428/40 |
| 4,934,996 | 6/1990 | Mohl et al. | 600/17 |
| 4,957,485 | 9/1990 | Andersson et al. | 604/96 |
| 5,001,825 | 3/1991 | Halpern | 29/456 |
| 5,007,434 | 4/1991 | Doyle et al. | 128/772 |
| 5,009,662 | 4/1991 | Wallace et al. | 606/192 |
| 5,021,045 | 6/1991 | Buckberg et al. | 604/53 |
| 5,024,668 | 6/1991 | Peters et al. | 606/194 |
| 5,031,613 | 7/1991 | Smith et al. | 128/207.14 |
| 5,033,998 | 7/1991 | Corday et al. | 600/18 |
| 5,041,093 | 8/1991 | Chu | 604/104 |
| 5,045,072 | 9/1991 | Castillo et al. | 604/280 |
| 5,047,018 | 9/1991 | Gay et al. | 604/164 |
| 5,091,205 | 2/1992 | Fan | 427/2 |
| 5,112,305 | 5/1992 | Barath et al. | 604/96 |
| 5,131,406 | 7/1992 | Kaltenbach | 128/772 |
| 5,158,545 | 10/1992 | Trudell et al. | 604/53 |
| 5,163,912 | 11/1992 | Gay et al. | 604/164 |
| 5,171,232 | 12/1992 | Castillo et al. | 604/280 |
| 5,173,346 | 12/1992 | Middleton | 428/53 |
| 5,180,368 | 1/1993 | Garrison | 604/104 |
| 5,196,024 | 3/1993 | Barath | 606/159 |
| 5,197,952 | 3/1993 | Marcadis et al. | 604/96 |
| 5,201,706 | 4/1993 | Noguchi et al. | 604/96 |
| 5,226,427 | 7/1993 | Buckberg et al. | 128/772 |
| 5,295,994 | 3/1994 | Bonutti | 606/192 |
| 5,308,325 | 5/1994 | Quinn et al. | 604/96 |
| 5,324,260 | 6/1994 | O'Neill et al. | 604/96 |
| 5,344,399 | 9/1994 | DeVries | 604/96 |
| 5,360,406 | 11/1994 | Boykin et al. | 604/170 |
| 5,385,548 | 1/1995 | Williams et al. | 604/96 |
| 5,395,331 | 3/1995 | O'Neill et al. | 604/96 |
| 5,401,244 | 3/1995 | Boykin et al. | 605/53 |
| 5,423,745 | 6/1995 | Todd et al. | 604/53 |
| 5,423,851 | 6/1995 | Samuels | 606/198 |
| 5,487,730 | 1/1996 | Marcadis et al. | 604/96 |
| 5,505,698 | 4/1996 | Booth et al. | 604/96 |

OTHER PUBLICATIONS

One page leaflet with Retrograde Coronary Sinus Perfusion Cannula and Pressure Sensing Syringe of DLP (undated).

Shanebrook et al.; "Vortex Mixing Catheter"; Medical & Biological Engineering & Computing; vol. 30 (1992) Jan., No. 1, pp. 123–124.

Directions for Use: Retrograde Coronary Sinus Perfusion Cannula; DLP, Inc. (1990).

Advertisement entitled "Together we bring medical innovations to the world" (2 pgs); from The Annals of Thoracic Surgery, vol. 56, No. 6, Dec. 1993 (DLP, Inc.).

Advertisement entitled "Introducing the Only ULTRA–SIL"; DLP; Journal of Thoracic & Cardiovascular Surg. (Jun. 1994).

Advertisement entitled "DLP Introduces the New Retrograde Coronary Sinus Perfusion Cannula"; (1 page) Journal of Thoracic & Cardiovascular Surg. (Nov. 1992).

Instructions for Use: Retroplegia Cannula of Research Medical, Inc. (4 pgs.) Nov. 25, 1991.

P. 8 and 9 from Research Medical, Inc. (RMI) annual report; reporting (among other things) "Patent Pending—Textured Retrograde Cardioplegia Balloon Surfaces" and Patent Pending—Retracta–Guard™ Retention Lumen for Cardioplegia Balloon Catheters.

Leaflet on Surgitek Venous Cannula for cardiovascular bypass surgery.

P. 12 from a price listing of Research Medical, Inc. for Retroplegia Coronary Sinus Perfusion Cannula.

Advertisement for "Vent Catheters" from Research Medical, Inc.

Brochure entitled "Looking for a Retrograde Cardioplegia Cannula with a Manually–Inflated, Textured Silicone Balloon?" (1 page) from Research Medical, Inc.

Brochure entitled "Retroplegia II—Coronary Sinus Cardioplegia Cannula with Retractaguard—Anti–Retraction Lumen" (2 pages) from Research Medical, Inc.

Brochure entitled "Retroplegia with Textured Balloon" (2 pages) from Research Medical, Inc.

P. 12–14 from a price listing of Research Medical, Inc. for Retroplegia Retrograde Cardioplegia.

Leaflet (3 pages) from USCI entitled "USCI 1967–68—Cardiology Radiology Surgery and Accessories".

Leaflet (3 pages) from American Cystoscope Makers, Inc. (ACMI) entitled "Catheters and Related Products".

2 sheets entitled "Urological Instruments" from C.R. Bard, Inc. (dated by PTO Jan. 26, 1940).

Menasche et al.; "La cardioplegie retrograde par le sinus coronaire"; Technique Chirurgicale; La Presse Medicale, 29 Nov. 1986 15, No. 42; pp. 2113–2114.

Brochure entitled "Sarns—Sterilized Disposable Instruments" Apr. 1984.

Bailey et al.; "Cardiac Surgery 1960–61" (1960).

Blanco et al.; "A Direct Experimental Approach to the Aortic Valve II. Acute Retroperfusion of the Coronary Sinus"; J. Thoracic Surg. Aug., 1956.

Fitch et al.; "Obturators for Extracorporeal Circulation Cannulae"; J. Thoracic Surg. May, 1959.

Page from The Annals of Thoracic Surgery, vol. 19, No. 3, Mar. 1975 entitled "Sarns Presterilized Atrial Vent Catheter and Left Vent Catheter".

One page from CH—Thoracic, Cardiovascular entitled Mayo Coronary Perfusion Components (Balloon Style) dated by PTO Aug. 16, 1988.

Zombolas et al.; "Retrograde coronary sinus perfusion: pressure monitoring"; Perfusion 1992; 7:291–294.

Menasche et al.; "Retrograde Coronary Sinus Perfusion: A Safe Alternative for Ensuring Cardioplegic Delivery in Aortic Valve Surgery"; The Annals of Thoracic Surgery, vol. 34, No. 6, Dec., 1982.

Buckberg; "Retrograde pulmonary venous pressure measurement—Fact or artifact?"; Journal of Thoracic and Cardiovascular Surgery, vol. 59, No. 3, Mar., 1970.

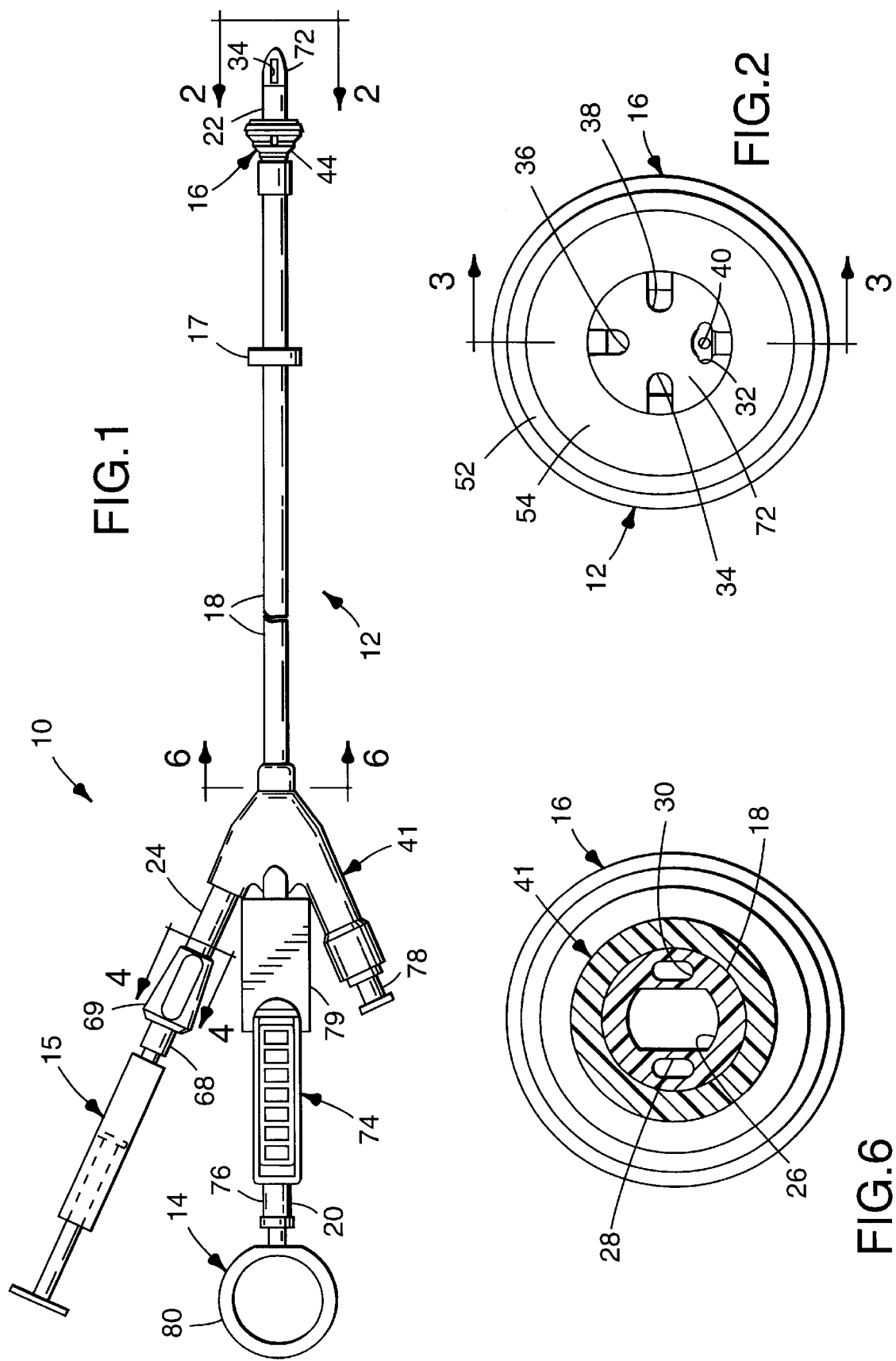

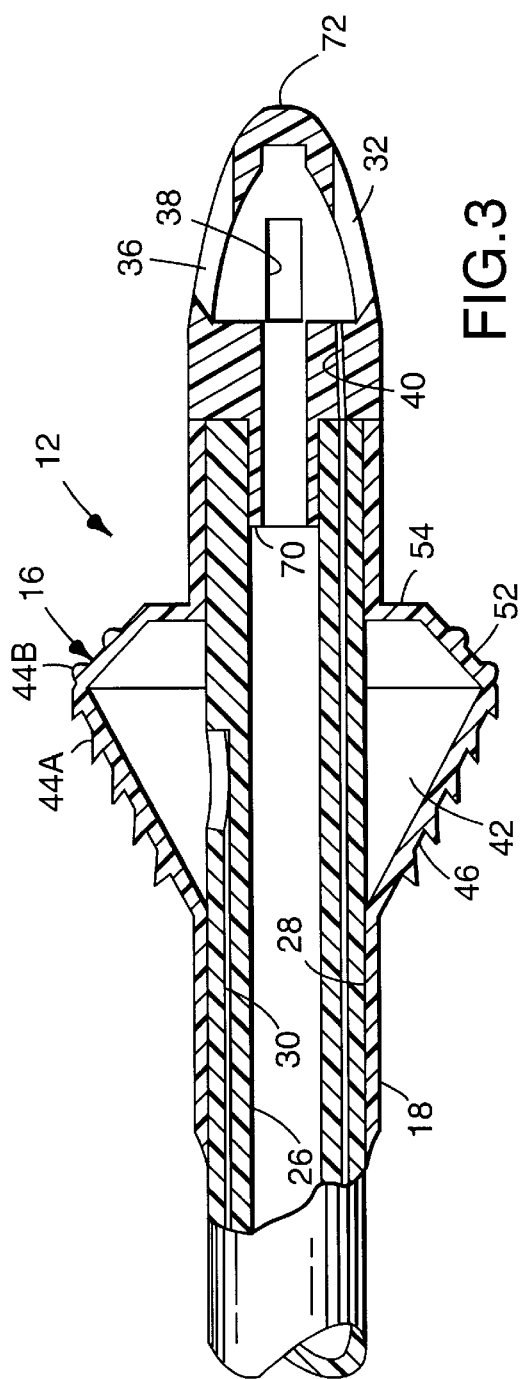
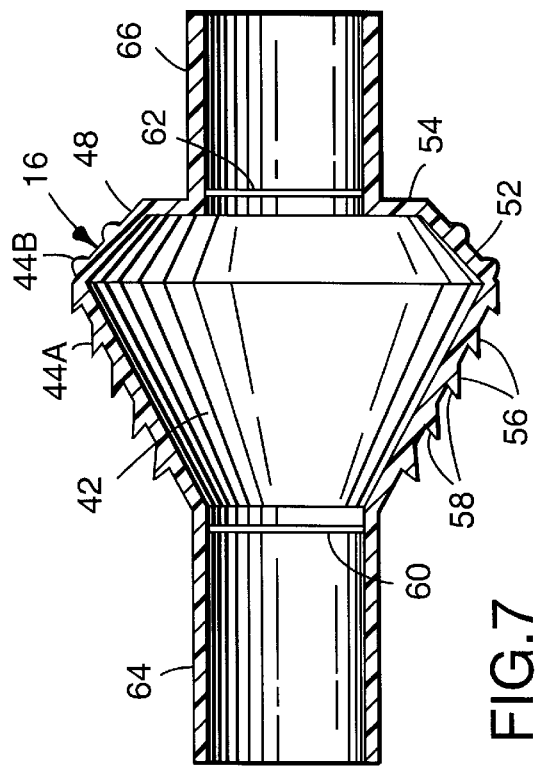

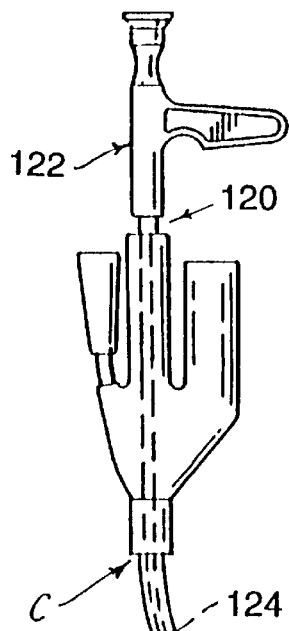
FIG. 12
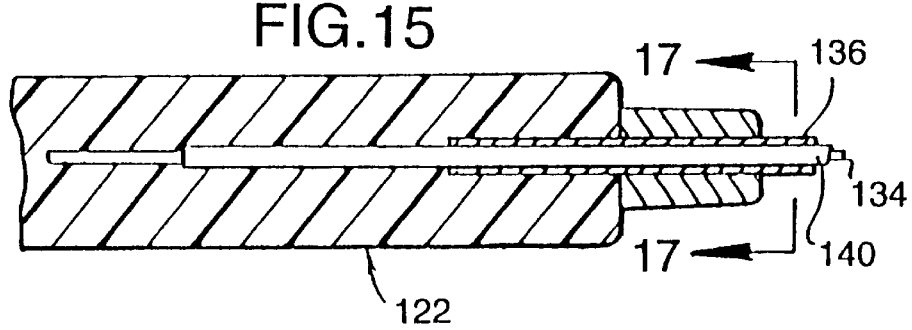
FIG. 15

RETROGRADE CORONARY SINUS CATHETER

This is a continuation of application Ser. No. 08/021,526, filed Feb. 23, 1993, now U.S. Pat. No. 5,395,331 which is a continuation-in-part of application Ser. No. 07/874,589, filed Apr. 27, 1992, now U.S. Pat. No. 5,324,260.

BACKGROUND OF THE INVENTION

This invention relates generally to a coronary sinus catheter and stylet assembly, and more particularly to a stylet and balloon catheter useful in the retrograde administration of cardioplegia through the coronary sinus.

Cardioplegia is a commonly used technique for protecting the heart during heart surgery. Typically, cooled cardioplegia solution (e.g., a potassium solution) is administered to the patient's heart in the antegrade direction through the patient's aorta. "Antegrade" refers to the direction of normal blood flow, and "retrograde" refers to the direction opposite of normal blood flow. The cardioplegia solution stops the heart and reduces its temperature to minimize damage to the heart during surgery.

In recent years, there has been increasing interest in administering cardioplegia in the retrograde direction (opposite of normal blood flow) via the coronary sinus. Such retrograde cardioplegia has been used with patients having critical coronary artery stenosis making diffusion of cardioplegia in the antegrade direction difficult and inefficient, and with patients suffering aortic valve disease. P. Menasche et al., "Retrograde Coronary sinus Perfusion: A Safe Alternative for Ensuring Cardioplegic Delivery in Aortic Valve Surgery", The Annals of Thoracic Surgery, Vol. 34, No. 6, pages 647–658 (December 1982). See, also, J. Solorzano et al., "Retrograde Coronary Sinus Perfusion for Myocardial Protection during Cardiopulmonary Bypass", The Annals of Thoracic Surgery, Vol. 25, No. 3, pages 201–208 (March 1978); and D. Lolley et al., "Myocardial Distribution of Asanguineous Solutions Retroperfused under Low Pressure through the Coronary Sinus", J. Cardiovascular Surg., 21:287–294. (1980).

One difficulty in administering cardioplegia via the coronary sinus is that the sinus walls are slippery, extensible and are tapered such that the sinus vessels become smaller in the direction in which a catheter is advanced into the sinus vessel. See, e.g., U.S. Pat. No. 4,927,412, at column 1, lines 7–23. Techniques that have been developed to help secure balloon catheters in the coronary sinus include having someone manually hold the catheter in position during the surgery, or tying the catheter in position with a purse-string suture.

Dislodgement of such balloon catheters has been a long-standing issue with cardiovascular surgeons, which has even limited acceptance of the retrograde procedure. Acceptance of one fairly new technique, the continuous administration of "warm" cardioplegia, has been limited due to concerns regarding the ability of currently available catheters to stay in place in the coronary sinus. Dislodgement of the catheter during administration of warm cardioplegia may go undetected with potentially serious consequences.

U.S. Pat. No. 4,927,412 (Menasche) discloses a coronary sinus catheter for use in administering cardioplegia solution in the retrograde direction via the coronary sinus. That catheter includes an elongate member, and a balloon mounted on the elongate member. The elongate member has at least two lumens including one lumen in fluid communication with the interior of the balloon. The balloon includes at least one truncated conical surface having outwardly-facing spaced-apart parallel concentric lands formed thereon for frictionally engaging the coronary sinus. That catheter does not include a pressure sensor on the balloon inflation line.

The balloon described in U.S. Pat. No. 4,927,412 (Menasche) is formed of silicone rubber having a hardness of approximately 50 on the Shore A scale. The lands of that balloon are generally hemispherical in cross section having a radius of approximately 0.015 inches (0.038 millimeters), and are spaced apart a distance of approximately 0.05 inches (1.27 millimeters). The wall thickness of that balloon is approximately 0.030 inches (0.762 millimeters).

The balloon described in U.S. Pat. No. 4,927,412 (Menasche) was particularly designed for use with an open atrium technique. In the "open atrium" technique, the right atrium of the heart is substantially opened up with a large incision (e.g., two inches (50 mm)) so that-direct access is provided to the coronary sinus. The distal end of the retrograde catheter is then inserted directly into the coronary sinus and the balloon is inflated to engage the walls of the coronary sinus.

While there are some advantages to the open atrium technique, one disadvantage is the inability to use a "Two-stage" venous catheter to drain the inferior vena cava and the right atrium. "Two-stage" venous catheters are sold under the trade designation "SARNS Two-Stage Venbus Return Catheter" by Minnesota Mining and Manufacturing Company, St. Paul, Minn. Such "Two-stage", catheters are inserted through a small incision into the right atrium until the smaller diameter distal end portion of the catheter is positioned in the inferior vena cava. The smaller diameter, distal portion of the "Two-stage" catheter drains venous blood from the inferior vena cava, and the larger diameter portion, which is immediately proximal the distal portion, drains blood from the right atrium. The drained blood is then supplied to the extracorporeal support circuit, where among other things it is oxygenated before being returned to the patient. In the "open atrium" technique, two catheters (in addition to the retrograde catheter) must be used to perform the same function as the "Two-stage" venous catheter.

Many surgeons prefer to use a "blind" procedure as opposed to the "open atrium" technique. Only a small incision is made to gain access to the right atrium and the coronary sinus with the "blind" technique. Advantages of the "blind" procedure include making a smaller incision and allowing the use of the "Two-stage" venous catheter. The balloon thickness and durometer specified in U.S. Pat. No. 4,927,412 result in a balloon that is stiff enough to be difficult to use-in the blind technique.

DLP, Inc., Grand Rapids, Mich., and RMI, Inc., Salt Lake City, Utah, sell retrograde catheters under the trade designations "dlp Retrograde Coronary Sinus Perfusion Cannula (Model Code No. 94015 (15 French))" and "RETROPLE-GIA Coronary Sinus Perfusion Cannula (Catalog Nos. RCS-014, RC-014-MIB and RC-014-MIBB)", respectively.

The "DLP" cannula comprises a wire-wound silicone rubber cannula body with a beveled tip. The DLP cannula includes an inflatable retention balloon mounted on the cannula body approximately ⅜ inches (10 mm) from the beveled tip, and an inflation assembly at the proximal end of the cannula for inflating the retention balloon. When not inflated, the "DLP" balloon has a very low, profile and conforms fairly closely with the surface of the cannula body.

The DLP inflation assembly consists of an expandable balloon in fluid communication with the inflatable retention balloon, and a one-way valve between the expandable balloon and a luer fitting adapted to receive a fluid syringe for inflating the retention balloon. The arrangement is such that the expandable balloon, which is visible in use, is expanded when the inflatable retention balloon, which is inside the coronary sinus in use, is inflated. This provides an indication of pressure in the retention balloon. The visible/expandable "DLP" balloon has a wall thickness of approximately 0.019 inches (0.48 mm).

The "DLP" inflatable retention balloon, after being cut open, was measured to have a wall thickness of 0.019 inches (0.48 millimeters) when not inflated. From this figure, the inflated "DLP" retention balloon was calculated to have a wall thickness of approximately 0.006 inches (0.15 millimeters) when inflated.

RMI sells at least three retrograde cannulae including (1) a 14 French cannula with a "self-inflating/deflating" retention balloon and an insertion stylet (Catalog No. RCS-014); (2) a 14 French cannula with a manually inflatable balloon and a malleable stylet (Catalog No. RC-014-MIP); and (3) a 14 French cannula with a manually inflatable balloon and a "Buckberg" stylet (Catalog No. RC-014-MIBB).

The manually inflatable balloon of the "RMI" catheter sold under Catalog No. RC-014-MIB, after being cut open, was measured to have a wall thickness of 0.017–0.019 inches (0.43–0.48 millimeters) when not inflated. From this figure, the inflated "RMI" balloon was calculated to have a wall thickness of approximately 0.006 inches (0.15 millimeters) when inflated. Like the, "DLP" balloon, that "RMI" balloon (Catalog No. RC-014-MIB) conforms fairly closely with the surface of the cannula when the balloon is not inflated.

One problem with both the "DLP" and "RMI" cannulae models with uninflated balloons that conform to the surface of the cannula is that the balloons when inflated tend to become displaced relative to the longitudinal axis of the cannula. This allows the distal end of the catheter to become displaced toward the walls of the coronary sinus.

U.S. Pat. No. 5,021,045, which may relate to RMI's "self-inflating/deflating" cannula sold under Catalog No. RCS-014, describes a retrograde cannula having a retention balloon which is filled with the infusion fluid via openings between the infusion lumen and the interior of the balloon. That balloon is "constructed so that it is not necessary for the balloon to expand significantly from its unfilled state in order to seal the coronary sinus." See, e.g., column 9, lines 3–9, of U.S. Pat. No. 5,021,045, As reported in U.S. Pat. No. 5,621,045, that balloon is formed of polyurethane, and has a wall thickness within the range of 0.003–0.005 (0.004) inches (0.076–0.127 mm (0.102 mm)).

U.S. Pat. No. 5,021,045 also describes a particular ratio of cross-sectional areas between the infusion lumen outlets and the openings between the balloon and the infusion lumen, which among other things is apparently necessary in order for the balloon to be self-filling. While U.S. Pat. No. 5,021,045 discusses avoidance of "jet-like flow" exiting the catheter by regulating the above ratio and boring the infusion lumens at an angle, it has been found that the RMI cannulae sold under Catalog Nos. RCS-014 and RC-014-MIB spray a thin stream of fluid through each outlet for a distance of several inches when saline solution is delivered through the infusion lumen and the cannula is held in air.

SUMMARY OF THE INVENTION

This invention provides a coronary sinus catheter particularly useful for the retrograde administration of cardioplegia solution into the coronary sinus of a patient's heart; which is particularly adapted for improved retention and stability in the coronary sinus; which in one aspect is designed to measure and display temperature at the catheter; which in another aspect is adapted to show when a vacuum is drawn on a retention balloon mounted adjacent the distal end of the catheter; and which in yet another aspect is adapted to provide a gentle, non-spraying flow of cardioplegia solution.

The catheter of the invention is adapted for use in either the "blind" or "open atrium" techniques, and is designed to maintain the retention balloon co-centric with the longitudinal axis of the catheter.

Generally, a catheter of the invention comprises a flexible, elongate catheter tube having proximal and distal ends, an inflatable balloon for securing the distal end of the catheter in the coronary sinus, and a pressure sensor tube for sensing pressure in the balloon to indicate the status of the balloon. The catheter tube includes infusion, pressure-sensing and inflation lumens extending longitudinally through the tube. At least one infusion lumen outlet is provided generally adjacent the distal end of the catheter tube, and at least one pressure-sensing lumen outlet is provided generally adjacent the distal end of the catheter tube. The balloon is positioned on the catheter tube generally adjacent the distal end of the catheter tube but proximally of the infusion lumen and pressure-sensing lumen outlets. One end of the inflation lumen is in fluid communication with the interior of the balloon for inflating the balloon. The balloon is molded of elastomeric material having a durometer in the range of 20 to 35 on the Shore A scale, and has a wall thickness in the range of 0.3–0.5 millimeters when not inflated. The balloon has a plurality of outwardly-facing, spaced-apart, segmented, annular ribs or lands for frictionally engaging the coronary sinus.

One end of the pressure sensor tube is in fluid communication with the end of the inflation lumen opposite the inflation balloon. The pressure sensor tube is formed of elastomeric material having a durometer greater than 35 on the Shore A scale, and has a wall thickness greater than 0.6 millimeters. The internal volume of the pressure sensor tube is relatively non-expansible relative to the internal volume of the inflation balloon in normal operation of the catheter. A connection device is provided in fluid communication with the end of the pressure sensor tube opposite the inflation lumen for connecting a pressurizing means to the catheter to inflate and/or deflate the inflatable balloon.

Preferably, the pressure sensor tube has a durometer in the range of 35–50 on the Shore A scale, and a wall thickness in the range of 0.6–1.3 millimeters. Most preferably, the balloon has a wall thickness when not inflated of approximately 0.33–0.48 millimeters, and the pressure sensor tube has a wall thickness of approximately 0.76–1.01 millimeters.

According to one aspect of the invention, each segmented annular rib or land comprises a plurality of raised rib portions separated by non-raised portions, with the raised rib portions and non-raised portions extending annularly around the periphery of the balloon in alternating fashion. In one preferred version, the raised rib portions of adjacent ribs or lands are staggered such that-the raised rib portions of one rib are generally longitudinally aligned with the non-raised portions of the adjacent rib or land. In another preferred version, the raised rib portions of generally adjacent ribs or lands are generally aligned in the longitudinal direction of the catheter, and the non-raised portions of generally adjacent ribs or lands are generally aligned in the longitudinal direction.

Preferably, the non-raised portions preferentially stretch in comparison with the raised rib portions as the balloon is inflated, thereby reducing stretching and distortion of the raised rib portions as the balloon is inflated.

Also, preferably, the raised rib portions have a generally asymmetrical profile along the longitudinal direction of the catheter, with the raised rib portions having an upper surface sloping smoothly and gradually forwardly to the surface of the balloon, and a back surface extending from the upper surface more steeply to the surface of the balloon than the upper surface slopes to the surface of the balloon.

Generally, the method of installing a coronary cannula according to this invention comprises providing a coronary cannula with a stylet extending through the lumen of the cannula. The stylet has a handle and a shaft that extends through the lumen with a stiff but flexible proximal portion, and a deformable distal portion. The shaft is sufficiently long that the deformable distal portion extends generally to the tip of the coronary cannula. The tip of the coronary cannula is then shaped by deforming the deformable distal portion of the stylet inside the lumen to facilitate its insertion through an incision in the right atrium and into the coronary sinus. The tip of the coronary cannula is then manipulated into the coronary sinus by steering the shaped tip by manipulating the handle. After the tip of the coronary cannula is in place, the cannula is anchored, for example by inflating a balloon at the tip of the cannula provided for that purpose, and the stylet can be drawn from the lumen of the coronary cannula.

Generally, the stylet apparatus for installing a coronary cannula according to this invention is adapted to fit inside the lumen of a coronary cannula to facilitate the installation of the cannula into the coronary sinus. The stylet comprises a handle, and a shaft extending from the handle and adapted to fit inside the lumen of the cannula. The shaft comprises a stiff but resilient proximal portion and a deformable distal portion that can be permanently deformed to a desired shape when inside the cannula to hold the tip of the cannula in a preselected shape to facilitate the insertion of the cannula into the coronary sinus. In the preferred embodiment the shaft comprises a malleable steel wire and a tube surrounding the proximal portion of the wire, stiffening the proximal portion of the shaft while leaving the distal portion of the wire uncovered. The deform able distal portion of the stylet is shorter than the stiffer proximal portion so that the deformability of the distal portion does not interfere with the steering of the tip, as described below. The distal portion of the stylet may be colored so that the surgeon can gauge the depth of penetration of the stylet and cannula in order to facilitate proper placement of the cannula.

The coronary cannula is preferably provided with the stylet already in the lumen, although they could be provided separately, and the stylet inserted into the lumen before the installation of the cannula. With the stylet inside the lumen of the coronary cannula, the tip of the coronary cannula can be configured to pass readily through an incision in the right atrium and into the coronary sinus. The malleable distal portion of the stylet holds the tip of the cannula in the desired preformed configuration, while the stiffer, flexible proximal portion of the stylet allows the cannula to flex and bend sufficiently as the tip of the cannula is manipulated into the coronary sinus.

The method of installing the coronary cannula and the stylet apparatus for installing the cannula allow the cannula to be quickly inserted into the coronary sinus for the prompt administration of cardioplegia solution. The stylet apparatus-also helps the surgeon gauge the depth of the tip to facilitate proper placement. The method and apparatus provide for the accurate placement of the cannula, and hold the cannula in place until it is anchored, for example by inflating a balloon on the cannula.

These and other advantages and features will be pointed out hereinafter.

BRIEF DESCRIPTION OF THE DRAWING

The invention will be further described with reference to the drawing wherein corresponding reference characters indicate corresponding parts throughout the several views of the drawing, and wherein:

FIG. 1 is a side view of the retrograde coronary sinus catheter of the invention;

FIG. 2 is a distal end view of the catheter of FIG. 1;

FIG. 3 is a longitudinal cross-sectional view of a distal end portion of the catheter of FIGS. 1 and 2 taken substantially along line 3—3 in FIG. 2;

FIG. 6 is a cross-sectional view substantially along line 6—6 of FIG. 1;

FIG. 7 is a longitudinal cross-sectional view through the inflatable balloon shown in FIGS. 1–2;

FIG. 12 is a view of a stylet constructed according to the principles of this invention, inserted in the lumen of the coronary cannula, shown as it would be used to manipulate the cannula into the coronary sinus;

FIG. 15 is an enlarged partial longitudinal cross-sectional view taken along the plane of line 15—15 in FIG. 13;

DETAILED DESCRIPTION OF A PREFERRED EMBODIMENT

Figure 4:
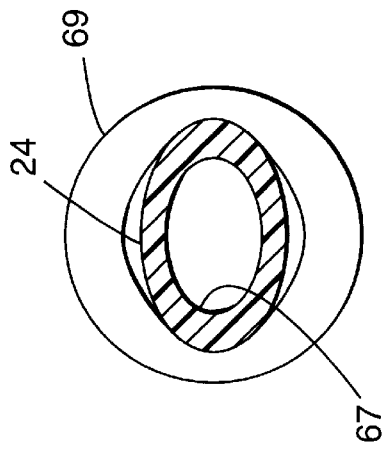
FIG. 4 is a cross-sectional view substantially along line 4—4 of FIG. 1, illustrating a pressure-sensing tube portion.

Now referring to the drawing, a coronary sinus catheter assembly of the invention is indicated in its entirety by the reference numeral 10. The coronary sinus assembly 10 includes a coronary sinus catheter 12, a malleable stylet 14 and a syringe 15 for inflating an inflatable balloon 16 mounted on the catheter 12. A preferred stylet 14 is described in co-assigned U.S. patent application Ser. No. 08/238,416, filed Apr. 28, 1994, which is a continuation of Ser. No. 07/979,010, filed Nov. 19, 1992, by Christopher M. Boykin and Thomas T. Vaalburg (incorporated herein by reference). An adjustable annular suture ring 17 may be provided along the catheter tube 18. The catheter 12 is a modified version of the catheter described in U.S. Pat. No. 4,927,412 (Menasche), which is incorporated herein by reference. The catheter 12 is particularly designed for the retrograde infusion of cardioplegia solution into the coronary sinus of a patient's heart. The catheter 12 is designed for use with either the "blind" or "open atrium" techniques.

As shown in FIG. 1, the catheter 12 generally comprises a flexible, elongate catheter tube 18 (e.g., 17 French) having proximal and distal ends 20 and 22, the inflatable balloon 16 which is adapted for retaining the distal end 22 of the catheter 12 in the coronary sinus, and a pressure or inflation sensor tube 24 for sensing pressure in the balloon 16 to indicate the status of the balloon 16. The pressure or inflation sensor tube 24 has an internal volume that is relatively non-expansible relative to the internal volume of the inflation balloon 16 in normal operation of the catheter 12.

As used herein, "proximal" and "distal" refer to opposite directions along the catheter 12. The "distal" direction is the direction (rightwardly in FIG. 1) toward the end 22 of the catheter 12 that is inserted in the coronary sinus. The "proximal" direction is the direction (leftwardly in FIG. 1) toward the end 20 of the catheter 12 which is connected to other components, such as tubing leading from a heat exchanger for cooling cardioplegia (not shown), of an extracorporeal support circuit (also not shown). Cardioplegia solution being delivered to the coronary sinus flows in the "distal" direction through the catheter 12. The proximal end of the catheter 12 will be indicated by the reference numeral 20.

The catheter tube 18 includes infusion, pressure-sensing and inflation lumens 26, 28 and 30 extending longitudinally through the catheter tube 18. At least one infusion lumen outlet, preferably four outlets 32, 34, 36 and 38, is/are provided generally adjacent the distal end 22 of the catheter tube 18. At least one pressure sensing lumen outlet 40 is provided generally adjacent the distal end 22 of the catheter tube 18. One end of the pressure sensor tube 24 is in fluid communication with the proximal end of the inflation lumen 30, which is the end opposite the inflation balloon 16.

The catheter tube 18 is preferably formed of silicone rubber material, and is flexible and resilient. As an alternative, the catheter tube 18 can be of the wire-reinforced type, which although it will be stiffer than the preferred version would still be flexible and resilient in normal use.

A three-way Y-type connection assembly 41 is mounted on the proximal end 20 of the catheter tube 18 to adapt the catheter 12 for connecting (1) the syringe 15 in fluid communication with the balloon-inflation lumen 30, (2) a cardioplegia'supply line (not shown) in fluid communication with the infusion lumen 26, and (3) a pressure sensing line (not shown) in fluid communication with the pressure-sensing lumen 28 to monitor pressure in the coronary sinus adjacent the distal tip 72 of the catheter 12.

The connection assembly 41 is molded of silicone material and is bonded to the catheter tube 18 by any suitable technique including silicone adhesive, such as available under the trade designation "LOCTITE 18188" from Loctite Corp., Newington, Conn. The pressure sensor tube 24 may be an integral molded part of the connection assembly 41.

The inflatable balloon 16 is mounted on the catheter tube 18 generally adjacent the distal end 22 of the catheter tube 18 proximally (leftwardly in FIG. 1) of the infusion lumen and pressure-sensing lumen outlets 32, 34, 36, 38 and 40. One end of the inflation lumen 30 is in fluid communication with the interior 42 of the balloon 16 for inflating the balloon 16. The balloon 16 has a generally pear-shaped cross-sectional profile along the longitudinal direction of the catheter tube 18.

The balloon 16 is molded of elastomeric material, such as silicone rubber, having a durometer in the range of 20 to 35 on the Shore A scale, and has a wall thickness in the range of 0.3–0.5 millimeters when not inflated. Most preferably, the balloon 16 has a wall thickness when not inflated of approximately 0.33–0.48 millimeters (e.g., 0.012–0.019 inches). For example, the wall thickness of the balloon 16 may be approximately 0.43 mm (0.017 inches), and the durometer is approximately 28 on the Shore A scale.

Suitable silicone rubber material for the balloon 16 includes a blend of the materials available under the trade designations "HE-26" and "HE-30" from Dow Corning Corp., Midland, Mich. The balloon 16 may be molded by using liquid injection molding (LIM), transfer molding or blow molding.

Figure 5:
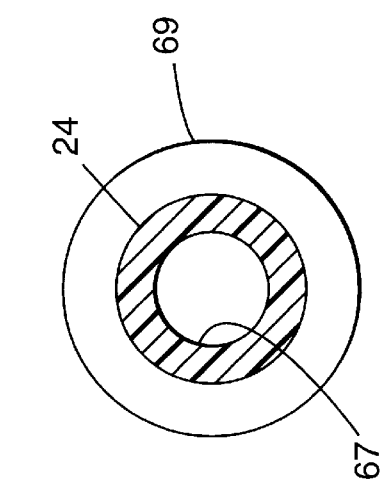
FIG. 5 is a cross-sectional view similar to FIG. 4 of the pressure-sensing tube portion, illustrating the cross-section of the pressure-sensing tube portion when the balloon is drawn down by vacuum.

The balloon 16 has a plurality of concentric outwardly-facing spaced-apart parallel lands or ribs 44 for frictionally engaging the coronary sinus. The balloon's normal, uninflated configuration is expanded outwardly from the catheter tube 18 such that the longitudinal cross-sectional profile of the balloon 16 is generally pear-shaped. The balloon 16 may be drawn inwardly from its normal configuration when a vacuum is drawn on the inflation lumen 30. The pressure sensor tube 24 is adapted to provide an indication (among other things) of whether a vacuum has been drawn on the inflatable balloon 16. FIG. 5 illustrates the pressure sensor tube 24 flattening out somewhat in response to vacuum.

As used herein, "vacuum" merely refers to the pressure in the interior 42 of the balloon 16 being less than the outside ambient pressure or local environmental pressure (e.g., pressure in the right atrium or coronary sinus). Normally, it is used to refer to the interior pressure of the balloon 16 being sufficiently low that the balloon 16 is drawn toward the catheter tube 18.

It is believed that drawing the balloon 16 inwardly toward the catheter tube 18 facilitates introducing the distal end 22 of the catheter 12 into the coronary sinus via the "blind" technique. In the "blind" technique, a small incision is made into the right atrium of the heart and the distal end 22 of the catheter 12 is introduced into the coronary sinus "blind" via the right atrium. In the "open atrium" technique as opposed to the "blind" technique, a large incision is made into the right atrium to allow direct access of the coronary sinus.

The profile of the balloon 16 includes a substantially conical proximal surface 46 tapering gradually down in the proximal direction (leftwardly in FIG. 1) to the surface of the catheter tube 18, and a distal surface 48 tapering at a higher average slope down in the distal direction (rightwardly in FIG. 1) to the surface of the catheter tube 18 or the distal tip 72 of the catheter 12. The balloon 16 is generally symmetrical around the longitudinal axis of the catheter tube 18. The proximal surface 46 tapers downwardly at an included angle of approximately 50 degrees from the maximum radius of the balloon 16 to the surface of the catheter tube 18.

As used herein, "included angle" refers to the angle formed between opposite sides of the conical surfaces, and is double the angle formed between the conical surface and the longitudinal axis of the catheter tube 18.

The distal surface 48 of the balloon 16 includes two portions: (1) a first (conical or frustoconical) portion 52 extending distally from the proximal surface 46 and tapering in the distal direction at an included angle of approximately 80 degrees; and (2) a second generally flat portion 54 extending between the outer circumferential surface of the distal tip 72 or catheter tube 18 adjacent the distal tip 72. The flat portion 54 is generally perpendicular to the longitudinal axis of the catheter tube 18.

The annular ribs 44 are formed on the proximal surface 46 and the conical portion 52 of the distal surface 48 of the balloon 16. As illustrated in FIG. 7, the ribs 44A formed along the proximal surface 46 of the balloon 16 are asymmetrical. The proximal ribs 44A include generally annular, outer surface portions 56 that are co-axial with the longitudinal axis of the catheter tube 18, and proximal surface portions 58 extending outwardly from the proximal surface 46 approximately at a right angle to the proximal surface 46 to the annular; outer surface portions 56. The juncture between the annular, outer surface portions 56 and the proximal surface portions 58 has a suitable radius, such as 0.005 inches (0.127 mm). Most preferably, there are five ribs 44A formed along the distal surface 48 of the balloon 16, and the five ribs 44A are spaced at approximately 0.07 inch (1.78 mm) intervals in the longitudinal direction of the catheter 12.

The annular ribs 44B formed along the conical portion 52 of the balloon's proximal surface 46 are preferably, generally symmetrical through their cross sections. The ribs 44B extend from the surface of the conical portion 52 approximately 0.02 inches (0.508 mm), and have a cross-sectional radius of approximately 0.03 inches (0.762 mm).

As shown in FIG. 7, the balloon 16 is provided with two annular glue rings 60 and 62 along tubular extensions 64 and 66, which serve to provide an even glue line between the tubular extensions 64 and 66 and the catheter tube 18. The even glue line is believed to help stabilize the balloon 16 to-maintain the balloon 16 centered around the catheter tube 18 as the balloon 16 is inflated. Suitable glue includes a silicone adhesive available under trade designation "LOCTITE 18188" from Loctite Corp., Newington, Conn., or the silicone adhesive available under the trade designation "WALKER 950".

The pressure sensor tube 24 is formed of elastomeric material having a durometer greater than 35 on the Shore A scale, and having a wall thickness greater than 0.6 millimeters. Preferably, the pressure sensor tube 24 has a durometer in the range of 35–50 on the Shore A scale, and a wall thickness in the range of 0.6–1.3 millimeters (0.025–0.05 inches). Most preferably, the pressure sensor tube 24 has durometer of 40 on the Shore A scale, and a wall thickness of approximately 0.76–1.01 millimeters (0.03–0.04 inches). For example, the pressure sensor tube 24 may have a wall thickness of 0.89 millimeters (0.035 inches).

The pressure sensor tube 24 may conveniently be formed of silicone rubber-material available under the trade designation "LSR 595" from Dow Corning Corp., Midland, Mich. by liquid injection molding ("LIM"), transfer molding or extrusion. The lumen 67 of the pressure sensor tube 24 may have a relaxed diameter (see FIG. 4) of approximately 0.25 inches (6.4 mm).

A connection device 68 is provided at the proximal end 20 of the catheter 12 in fluid communication with the proximal end of the pressure sensor tube 24, which is the end opposite the inflation lumen 30. The connection device 68 is adapted for connecting a pressurizing means, such as the syringe 15, to the catheter 12 to inflate and/or deflate the inflatable balloon 16.

The syringe 15 also permits a vacuum to be drawn on the balloon 16 as discussed above to draw the balloon 16 inwardly toward the catheter tube 18. The syringe 15 is preferably filled with saline solution, which is not compressible, although air could also be used. It is contemplated that the syringe would have an internal volume of 3 cc, and that up to 5 cc of fluid volume could be introduced into the balloon 16, inflation lumen 30 and pressure sensor tube 24.

A valve 69 is provided between the connection device 68 and the pressure sensor tube 24. The valve 69 is designed to prevent flow or escape of fluid through the valve 69, except when the male luer fitting of the syringe 15 is inserted into the connection device 69. When the luer fitting of the syringe 15 is mounted in the connection device 68, the valve 69 opens to allow delivery of fluid from the syringe 15 to the balloon 16 or withdrawal of fluid from the balloon 16 by drawing vacuum With the syringe 15. The valve 69 allows the syringe 15 to be withdrawn, with fluid being sealed in the balloon 16, inflation lumen 30 and pressure sensor tube 24.

In another preferred aspect of the invention, the infusion lumen 26 includes a constricted portion 70 (FIG. 3) spaced from the infusion lumen outlets 32, 34, 36 and 38. The total cross-sectional area of the infusion lumen outlet(s) 32, 34, 36 and 38 is substantially greater than the cross-sectional area of the constricted portion 70 of the infusion lumen 26 so that fluid exiting the infusion lumen outlets 32, 34, 36 and 38 is decelerated relative to its velocity through the constricted portion 70 of the infusion lumen 26. For example, the total cross-sectional areas of the infusion lumen outlets 32, 34, 36 and 38 may be approximately 16.8 mm$^2$; the cross-sectional area of the constricted portion 70 may be approximately 1.8 mm$^2$; and the typical cross-sectional area of the infusion lumen may be 3.25 mm$^2$.

Preferably, the molded distal tip 72 is soft and rounded-conical and has a closed end. As used herein, "rounded-conical" refers to a generally conical structure in which the surfaces may be smoothly rounded instead of tapering at a constant angle.. The infusion lumen outlets 32, 34, 36 and 38 comprise a plurality of elongate outlet slots (also 32, 34, 36 and 38) formed in the distal tip 72. The elongate slots 32, 34, 36 and 38 are spaced approximately equally around the circumference of the distal tip 72. The pressure-sensing lumen outlet 40 opens into one of the elongate outlet slots 32. The distal tip 72 is conveniently molded of silicone rubber material having a durometer of approximately 50 on the Shore A scale.

The constricted portion 70 may be formed by a reduced diameter tubular extension of the molded distal tip 72 extending into the catheter tube 18. The inside diameter of the constricted portion 70 may be approximately 0.06 inches (1.52 mm). The internal space formed between the infusion lumen outlets 32, 34, 36 and 38 and the constricted portion 70 preferably has a cross-sectional area greater than the cross-sectional area of the constricted portion 70.

In yet another preferred aspect of the invention, a temperature sensing strip 74 (FIG. 1) is provided along the infusion-lumen 26 generally adjacent the proximal end 23 of the catheter 12. The temperature sensing strip 74 includes liquid crystal display means (also 74) on the catheter 12 for displaying the temperature of the fluid being infused. Preferably, duplicate display means 74 are provided along opposite sides of the catheter 12. Temperature sensing strips of suitable type are available from American Thermometer Co., Glenview, Ill. It is believed that the temperature sensing strip 74 will be a significant convenience for the surgeon, allowing direct reading of the temperature of the cardioplegia solution without-looking away from the surgical field.

The temperature sensing strip 74 conveniently has an operating range between 4–40 degrees Celsius. A plurality of indicia may be provided on the temperature sensing strip 74 to indicate various temperature points. The indicia on the strip 74 may be of the type comprising a plurality of small sections of temperature sensitive material arranged along the temperature sensing strip 74 which change color according to their temperature.

For example, seven sections corresponding to temperature values of 4, 7, 10, 13, 34, 37 and 40 degrees Celsius could be provided on each display means 74. The sections corresponding to 4, 7, 10 and 13 degree Celsius values are framed by the color blue, and the sections corresponding to 34, 37 and 40 degrees are framed by the color red. If the temperature is exactly 10 degrees Celsius, the 10 degree Celsius section would turn a bright turquoise color. A straw color in that section would indicate a temperature slightly above the value displayed in that small section, and a royal blue color in that section would indicate a temperature slightly below the value displayed.

A suitable connection device is provided on the proximal end 23 of the temperature sensing strip 74 for connecting a cardioplegia supply line (not shown) in fluid communication with the infusion lumen 26. For example, the connection device may comprise a suitable locking female luer fitting 76. A similar connection device (e.g., a locking female luer fitting 78) may be provided at the proximal end of the pressure-sensing lumen 28 for connecting a pressure sensing line (not shown) in fluid communication with the pressure-sensing lumen 28.

A clamp 79, such as a pinch clamp 79 of conventional design, is provided on the connection-assembly 41 along the infusion lumen 26 between the catheter tube 18 and the temperature sensing strip 74. The clamp 79 allows manual control of cardioplegia solution flow through the catheter 12, as well as manual closing of the infusion lumen 26 to stop delivery of cardioplegia solution.

The stylet 14 includes malleable wire, and is deformable to set bends therein. Preferably, the stylet 14 is formed by coating the malleable wire with plastic material. As shown in FIG. 1, a ring 80 may be provided on the proximal end of the stylet 14 for grasping the stylet 14 with a finger, either for removal from the catheter 12 or to facilitate manipulating the catheter assembly 10 to insert the distal end 22 of the catheter 12 into the coronary sinus. The ring 80 may be molded of suitable plastic resin material.

Figure 8:
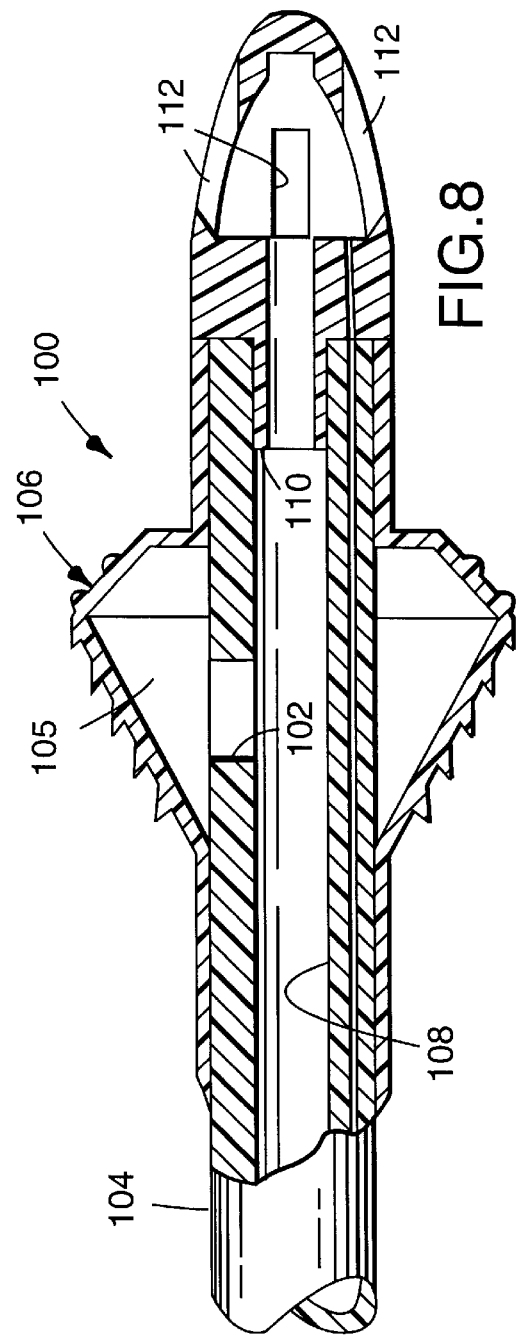
FIG. 8 is a longitudinal cross-sectional view similar to FIG. 3 illustrating an alternative, autoinflating embodiment of the balloon catheter.

As illustrated in FIG. 8, an alternative catheter designated generally 100 has at least one balloon-inflating opening 102 formed in the catheter tube 104 between the interior 105 of the balloon 106 and the infusion lumen 108. In this embodiment, a constricted portion 110, similar to constricted portion 70, is positioned along the infusion lumen 108 between the balloon-inflating opening 102 and the infusion lumen outlet 112. The constricted portion 110 is adapted to create back pressure in the infusion lumen 108 to automatically inflate the balloon 106 when fluid is being infused through the catheter 100. Other features of catheter 100 are similar to catheter 12 described above, with one exception being that catheter 100 lacks a separate inflation lumen.

Figure 9:
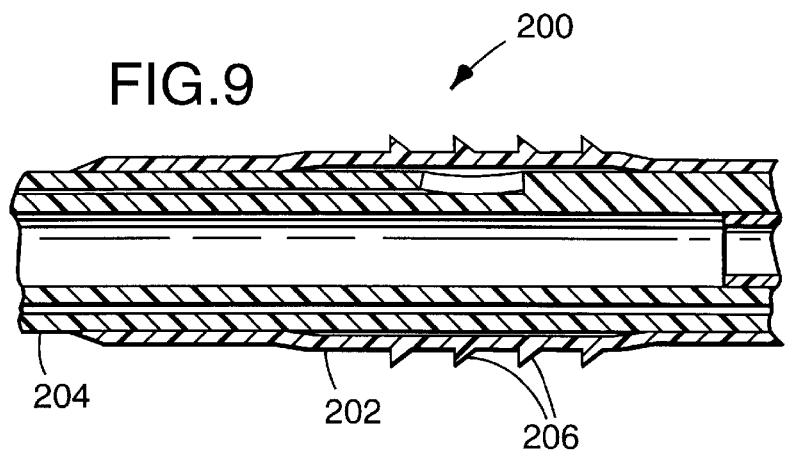
FIG. 9 is a longitudinal cross-sectional view similar to FIGS. 3 and 8 but further cut away, illustrating yet another alternative embodiment of the balloon catheter.

As illustrated in FIG. 9, a second alternative catheter designated generally 200 has an inflatable balloon 202 which lays flat against the outer surface of the catheter tube 204 when the balloon 202 is not inflated. The balloon 202 is provided with a plurality (e.g., 4) of annular lands or ribs 206 that are similar in many respects to ribs 44A of balloon 16. The ribs 206 of this alternative embodiment are asymmetrical in a fashion similar to ribs 44A. Other features of catheter 200 are similar to catheter 12.

Figures 10, 11:
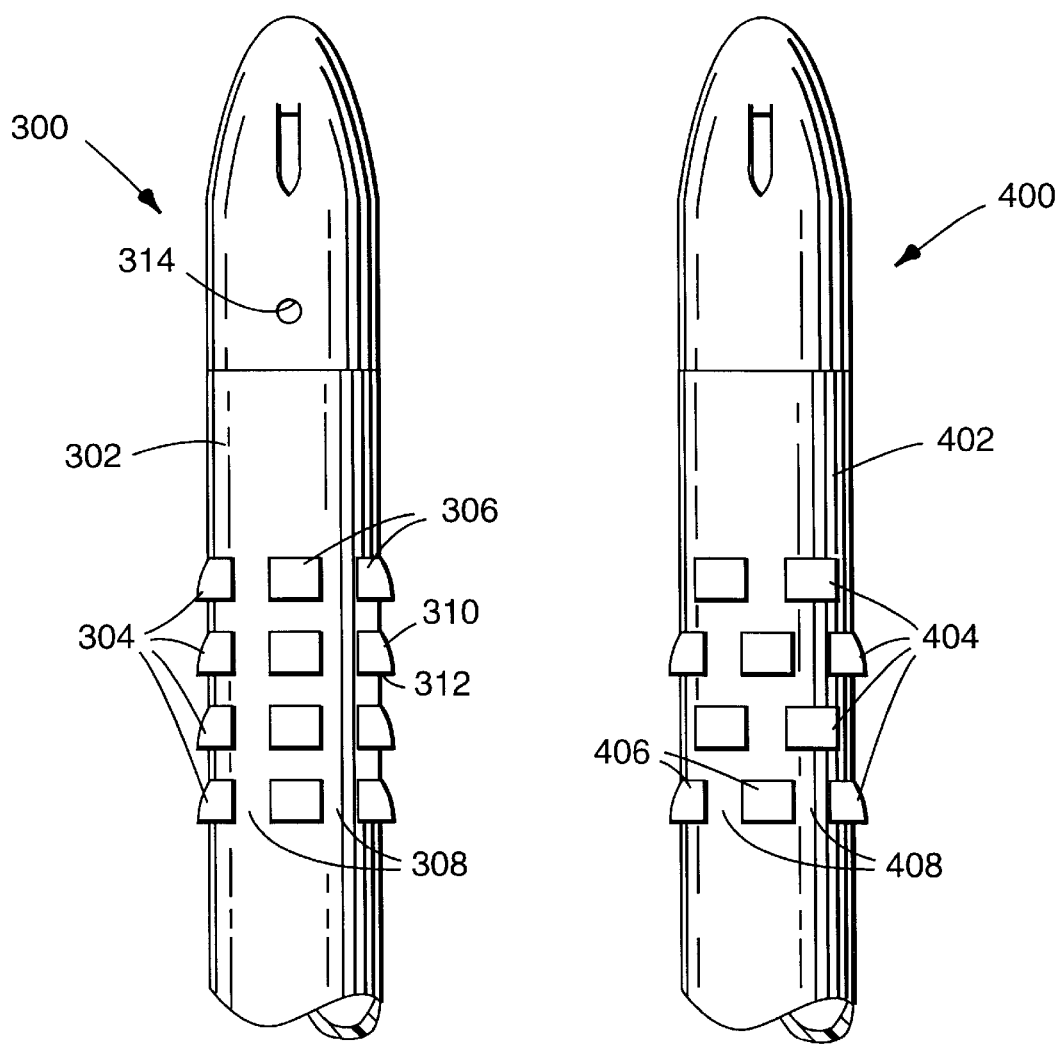
FIG. 10 shows the distal portion of another embodiment of the coronary sinus catheter.
FIG. 11 shows the distal portion of yet another embodiment of the coronary sinus catheter, similar in some respects to the catheter of FIG. 10.
Figure 13:
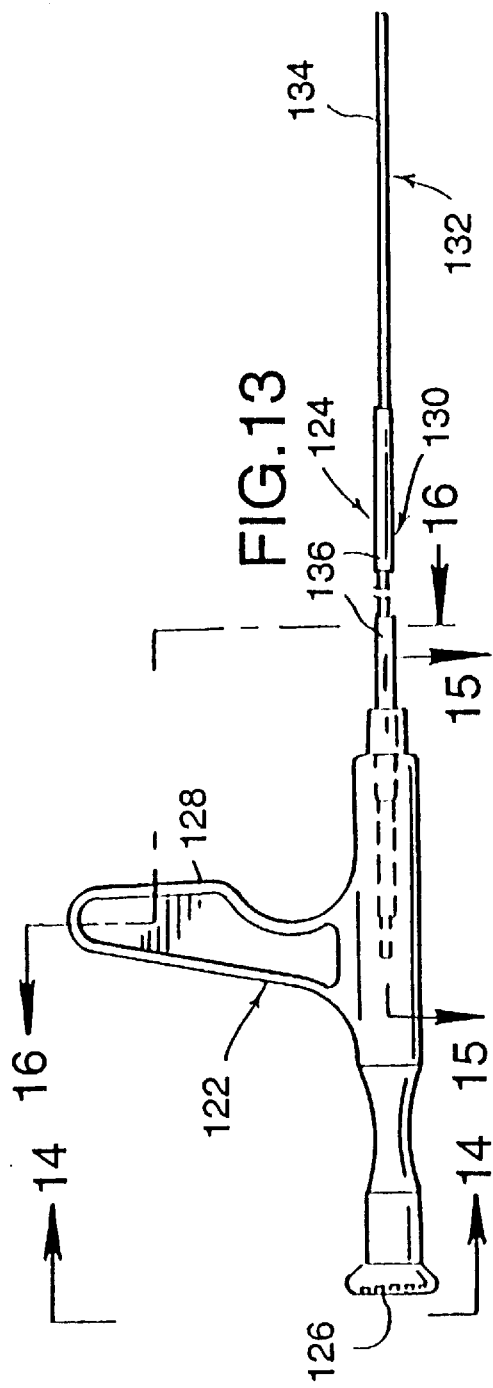
FIG. 13 is a partial side elevation view of the stylet.
Figure 16:
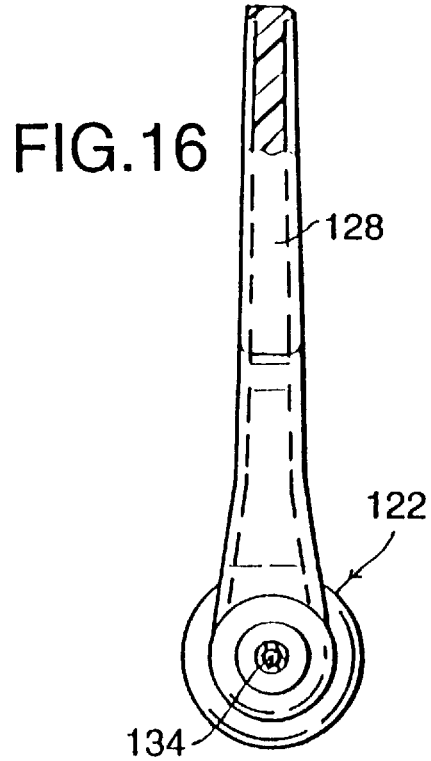
FIG. 16 is a vertical cross-sectional view of the stylet taken along line 16—16 in FIG. 13.
Figure 17:
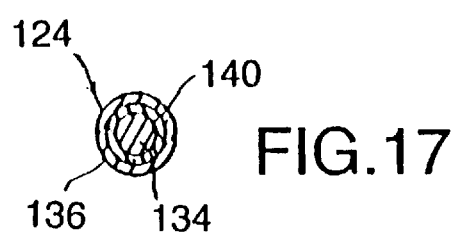
FIG. 17 is a vertical cross-sectional view of the stylet taken along the plane of line 17—17 in FIG. 15.
Figure 14:
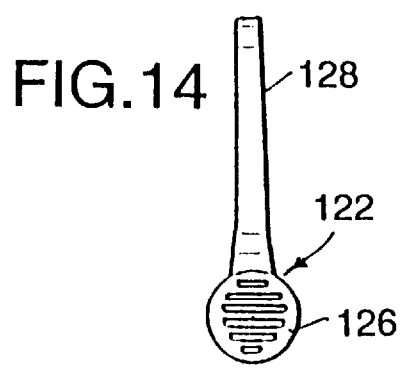
FIG. 14 is an end elevation view of the stylet taken along the plane of line 14—14 in FIG. 13.

FIG. 10 illustrates another embodiment of the coronary sinus catheter of the invention, here designated 300. The coronary sinus catheter 300 includes a balloon 302 having a plurality of outwardly-facing, spaced-apart, segmented, parallel, annular ribs or lands generally indicated at 304 for frictionally engaging the coronary sinus, but is otherwise similar to the catheter 200 in FIG. 9. As an alternative, the segmented-rib balloon catheter could be formed in the profile of FIGS. 1, 3, 7 and 8, and be of the type including a balloon-inflating opening, similar to the embodiment of FIG. 8, that allows infusion fluid to inflate the balloon 302.

The segmented ribs or lands are preferably integrally molded with the balloon 302 of generally elastomeric silicone material. Each segmented rib or land 304 comprises a plurality of solid raised rib portions 306 separated by non-raised portions 308, with the raised rib portions 304 and non-raised portions 308 extending annularly around the balloon 302 in alternating fashion. The raised rib portions 306 of adjacent ribs or lands 304 are generally aligned along the longitudinal direction of the catheter 300, and the non-raised portions 308 of adjacent ribs or lands 304 are generally aligned along the longitudinal direction of the catheter 300.

The balloon 302 preferably is expandable from an un-inflated diameter (FIG. 10), generally equal to the diameter of the catheter tube and closely conforming to the catheter tube, to an inflated diameter (not shown), substantially greater than the diameter of the catheter tube. The balloon 302 is at its un-inflated diameter for introducing the catheter 300 into the coronary sinus, and is inflated to its inflated diameter to secure the distal end of the catheter 300 in the coronary sinus.

Preferably, the non-raised portions 308 preferentially stretch in comparison to the raised rib portions 306 as the balloon 302 is inflated. The arrangement is such as to reduce stretching and distortion of the raised rib portions 306 to help them maintain, or reduce distortion from, their original profile as the balloon 302 is inflated.

Also, preferably, the raised rib portions 306 have a generally asymmetrical profile along the longitudinal direction of the catheter 300. The raised rib portions 306 have an upper surface 310 sloping smoothly and gradually forwardly to the surface of the balloon 302, and a back surface 312 extending from the upper surface 310 more steeply to the surface of the balloon 302 than the upper surface 310 slopes to the surface of the balloon 302.

Most preferably, three to seven (e.g., six) segmented ribs or lands 304 are provided on the balloon 302. Four segmented ribs or lands 304 are shown in FIG. 10. Each segmented rib or land 304 has the same number of raised rib portions 306 and non-raised portions 308 as the other ribs or lands 304. For example, each segmented rib or land 304 may include eight raised rib portions 306, and eight non-raised portions 308.

FIG. 10 also illustrates a pressure sensing lumen outlet 314 extending out through the circumference of the catheter 300 as opposed to into a infusion lumen outlet as illustrated in FIG. 3.

FIG. 11 illustrates yet another embodiment of the coronary sinus catheter, here designated 400, similar in many respects to catheter 300 shown in FIG. 10. Like catheter 300, the coronary sinus catheter 400 comprises a balloon 402 having segmented ribs or lands 404 formed by a plurality of raised rib portions 406 and non-raised portions 408 extending in alternating fashion around the periphery of the balloon 402. In contrast to catheter 300, the raised rib portions 406 of adjacent ribs or lands 404 are staggered such that the raised rib portions 406 are generally longitudinally aligned with the non-raised portions 408 of the adjacent rib or land 404.

FIGS. 12–17 illustrate details of a preferred stylet, here designated 120, for use with the coronary sinus catheter, which is designated "C" in FIGS. 12–17. The stylet 120 comprises a handle 122 and a shaft 124 extending from the handle 122 and adapted to fit inside the lumen L of the coronary cannula C. (See FIG. 12). In practice, the coronary cannula C can be provided premounted on the shaft 124 of a stylet 120, to facilitate the proper installation of the cannula C in the coronary sinus. Alternatively the stylet 120 and the cannula C could be provided separately.

The handle 122 of the stylet 120 may have a flat base 126 and a finger grip 128. Of course some other style of handle could be provided. The handle 122 is preferably made from a molded plastic, such as ABS, although the handle 122 could be made from any other suitable material.

The shaft 124 of the stylet 120 preferably has a stiff but flexible proximal portion 130, and a shorter, malleable distal portion 132. As noted above, the shaft 124 is sized to fit in the lumen L of a coronary cannula C, and is sufficiently long that the distal end of the shaft 124 is closely adjacent to, but does not protrude from, the distal end of the coronary cannula C. (See FIG. 12). The distal portion 132 of the shaft 124 is sufficiently malleable that it can be shaped by hand to a configuration to facilitate the insertion of the cannula C and stylet 120 into the coronary sinus, yet the distal portion 132 is sufficiently stiff to substantially retain this shape as the tip of the cannula C and stylet 120 are manipulated into the coronary sinus. The proximal portion 130 of the shaft 124 is sufficiently stiff to allow the tip of the stylet 120 and cannula C to be steered by manipulating the handle 122. The proximal portion 130 is preferably not so rigid that it cannot be deformed by hand, for-example to form a large radius arc in the proximal portion 130 to facilitate installation of the cannula C. The relative lengths of the proximal and distal portions 130 and 132 are important to the steerability of the stylet 120 and cannula C. The distal portion 132 of the stylet 122 must be sufficiently long to hold the shape of the tip of the cannula mounted on the stylet 120. However, the distal portion 132 must be sufficiently short so that the cumulative effect of the flexibility of the distal portion 132 does not unduly interfere with the ability to steer the stylet 120 and cannula C. The distal portion 132 is preferably shorter than the proximal portion 130, and is preferably between 1.5 and 6 inches (3.8 and 15.2 cm) long and most preferably between about 2 and 3 inches (5.1 and 7.6 cm) long. The proximal portion 130 is preferably between about 9 and 10 inches (22.9 and 25.4 cm) long so that the overall length of the shaft 124 is about 12 inches (28.5 cm).

The shaft 124 preferably comprises a long, malleable wire 134 extending from the handle 122. The wire 134 is preferably made of a medical grade stainless steel, such as an SS 303 or SS 304 stainless steel, or other suitable material. The wire 134 is dead soft (annealed), and of sufficient diameter that the wire 134 can be easily shaped by hand into a desired configuration yet hold its shape while the cannula C and stylet 120 are manipulated into the coronary sinus. The wire 134 preferably has a stiffness of between about 0.005 in/in and 0.025 in/in (most preferably 0.01–0.02 in/in (e.g., 0.015 in/in)) as determined by a standard Tenius-Olsen stiffness test with a 30 gram weight at a 0.75 inch deflection. See Federal Military Specification GGN-196, incorporated herein by reference, regarding Tenius-Olsen testing. The appropriate diameter may vary, depending on the size of the cannula C and the type of material used. For an SS 303 or 304 stainless steel a diameter of 0.040 inches (0.1016 cm) has been found to be satisfactory. The wire 134 must be sufficiently stiff to retain its shape, but it must be sufficiently flexible to be comfortably manipulated by the surgeon by hand without damaging the cannula C. Also the wire 134 must not be so stiff that it can puncture the tissue surrounding the coronary sinus.

An advantage of the malleable wire 134 is that for a given tip sharpness, the greater the flexibility, the greater force required to penetrate a given structure, for example the wall of the coronary sinus. Penetration pressure can be measured using an Instron Stress Machine to push a test piece through a standard medium, such as a 3 mm or 5 mm thick polyethylene sheet. The inventors conducted such tests measuring the puncture pressure at 3 inches from the tip when formed in a "C" and 6 inches from the tip and found that the average puncture pressure for ten repetitions is significantly higher with inventors' compound stylet 120. This means that greater force can be applied to the inventors' stylet 120 without puncturing the heart tissue.

The proximal portion of the wire 134 (i.e., the portion adjacent the handle 122) is surrounded by a tubular sheath 136. The sheath 136 stiffens the proximal portion of the wire 134, forming the relatively stiff proximal portion 130 of the shaft 124. For a wire diameter of about 0.040 inches (0.1016 cm), the sheath 136 can be a 14 gauge stainless steel tube. Of course, with different wire diameters, different tube gauges can be used. The section of the wire 134 covered by the sheath 136 forms the stiff but flexible proximal portion 130. The compound construction with the wire 134 extending through the sheath 136 prevents the proximal portion 130 from kinking. The distal portion 132 of the wire 134 protruding from the sheath 136 forms the malleable distal portion 132 of the shaft. The compound construction of the shaft 124 is relatively simple and inexpensive to manufacture. The fact that the wire 134 extends the length of the shaft 124 reduces the risk that the distal portion 132 will break off or separate from the shaft 124.

The wire 134 preferably has a coating 140, which may be a nylon, such as "ZYTEL 408™", or other suitable plastic. "ZYTEL 408™" is a trademark used in connection with a nylon resin available from E.I. Du Pont De Nemours & Company, Wilmington, Del. The coating 140 is preferably colored so that it is visible through the walls of the cannula C in which it is placed. The color of the coating 140 provides an indication of the depth of penetration of the tips of the cannula C and stylet 120 into the heart atrium, which helps to indicate when the tip of the cannula C is properly placed. At the point where the colored coating is no longer visible, the surgeon knows that the tips of the cannula C and stylet 120 are at a depth corresponding to the length of the proximal portion 130. This helps the surgeon to avoid inserting the cannula C past the coronary sinus, and possibly damaging the heart.

The entire stylet 120 is preferably coated with a silicone-based lubricant to facilitate the removal of the stylet 120 after the cannula C is properly placed in the coronary sinus. The lubricant allows the stylet 120 to be withdrawn without pulling the coronary cannula C from the heart. The coating 140 also facilitates the removal of the deformed distal portion 132 from the cannula C with a minimum of disruption.

OPERATION

A coronary cannula C is preferably provided in a sterile package, already mounted on the shaft 24 of a stylet 20. The surgeon bends the tip of the cannula C, deforming the distal portion 132 of the shaft 24, to the desired configuration to facilitate the installation of the cannula C in the coronary sinus. The distal portion 132 deforms to hold the end of the coronary cannula C in the desired shape.

To insert the catheter 12 into the heart via the "blind" technique, the right atrium is sutured and the distal end 22 of the catheter 12 (with the stylet 14 or 120 therein) is inserted through a small incision (in the area defined by the suture) into the right atrium. By placing a finger at the junction of the inferior vena cava and the atrio-ventricular groove, the distal end 22 of the catheter 12 can be guided into the coronary sinus. It may be helpful to gently lift the diaphragmatic aspect of the right ventricle to unfold the coronary sinus. The position of the catheter tip 72 can be verified by palpating the tip. In addition, the amount of colored coating 140 that is visible through the wall of the cannula C indicates to the surgeon the depth of the cannula tip in the heart.

The balloon 16 should be inflated slowly with approximately 3 cc of saline solution, the stylet 14 removed from the catheter 12, and the pinch clamp 79 closed. The lubricant coating facilitates the removal of the stylet 20 from the coronary cannula C with a minimum of disruption to the cannula C. The suture can then be tightened and the catheter 12 secured. The pinch clamp 79 may then be opened, all air removed, and lines attached to the connection device 76 for the infusion lumen 26 and the connection device 78 for the pressure-sensing lumen 28.

Cardioplegia solution may then be infused into the coronary sinus through the catheter 12. The pressure in the coronary sinus should be carefully monitored. Due to the deceleration of fluid after passing the constricted portion 72, flow through the infusion lumen outlets 32, 34, 36 and 38 is gentle and non-spraying. The surgeon may directly view the temperature sensing strip 74 to determine the temperature of the cardioplegia solution, or to verify information provided orally by the perfusionist.

As various changes could be made in the above constructions without departing from the scope of the invention, it is intended that all matter contained in the description above or shown in the accompanying drawing shall be interpreted as illustrative and not in a limiting sense.

We claim:

1. A coronary sinus catheter for the retrograde infusion of cardioplegia solution into the coronary sinus of a patient's heart, the catheter comprising:
   a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of cardioplegia solution to the catheter; and
   an inflatable balloon on the catheter tube generally adjacent the distal end of the catheter tube proximally of the infusion lumen outlet, the inflatable balloon being expandable as the balloon is inflated from an un-inflated diameter, approximately equal to the outer diameter of the catheter tube for introducing the catheter into the coronary sinus, to an inflated diameter, substantially greater than the outer diameter of the catheter tube for securing the distal end of the catheter in the coronary sinus;
   the inflatable balloon having a plurality of outwardly-facing, spaced-apart, segmented, annular ribs or lands for frictionally engaging the coronary sinus, each segmented annular rib or land comprising a plurality of solid, raised, elongate rib portions separated by non-raised portions extending annularly around the periphery of the balloon in alternating fashion, the non-raised portions preferentially stretching in comparison to the raised rib portions as the balloon is inflated to its inflated diameter, the balloon, including the ribs or lands, being integrally molded of generally uniform elastomeric material, each raised rib portion having a non-conical upper surface sloping smoothly and gradually toward the surface of the balloon.

2. A retrograde coronary sinus perfusion cannula that comprises:
   an elongate flexible tube with a central infusion lumen and an integral side lumen for pressure monitoring, the tube having a distal end and a proximal end;
   an inflatable cuff that encircles the tube adjacent the distal end of the tube, the inflatable cuff being formed of elastomeric material and having a plurality of outwardly-facing, spaced-apart, segmented, annular ribs or lands integrally molded with the cuff for frictionally engaging the coronary sinus, each segmented annular rib or land comprising a plurality of solid raised rib portions separated by non-raised portions extending annularly around the periphery of the cuff in alternating fashion, each raised rib portion having a non-conical upper surface sloping smoothly and gradually toward the surface of the cuff; and
   an introducer stylet removably received into the proximal end of the central lumen, the introducer stylet having a handle, a relatively rigid proximal portion adjacent the handle, and a relatively flexible shape-retaining distal portion remote from the handle.

3. A retrograde coronary sinus perfusion cannula according to claim 2 wherein the relatively flexible shape-retaining distal portion comprises malleable wire.

4. A retrograde coronary sinus perfusion cannula that comprises:
   an elongate flexible tube with a central infusion lumen and an integral side lumen for pressure monitoring, the tube having a distal end and a proximal end;
   an inflatable cuff that encircles the tube adjacent the distal end of the tube, the inflatable cuff being formed of elastomeric material and having a plurality of outwardly-facing, spaced-apart, segmented, annular ribs or lands integrally molded with the cuff for frictionally engaging the coronary sinus, each segmented annular rib or land comprising a plurality of solid raised rib portions separated by non-raised portions extending annularly around the periphery of the cuff in alternating fashion; and
   an introducer stylet removably received into the proximal end of the central lumen, the introducer stylet having a handle, a relatively rigid proximal portion adjacent the handle, and a relatively flexible shape-retaining distal portion remote from the handle;
   the direction longitudinally along the catheter tube from its proximal end toward its distal end constituting the forward direction, and the raised rib portions having a generally asymmetrical profile along the longitudinal direction of the cannula, the raised rib portions having an upper surface sloping smoothly and gradually forwardly to the surface of the cuff, and a back surface extending from the upper surface more steeply to the surface of the cuff than the upper surface slopes to the surface of the cuff.

5. A retrograde coronary sinus perfusion cannula according to claim 4 wherein the tube has an outer diameter, and the inflatable cuff is expandable from an un-inflated diameter, generally equal to the outer diameter of the tube for introducing the cannula into the coronary sinus, to an inflated diameter, substantially greater than the outer diameter of the tube for securing the distal end of the cannula in the coronary sinus.

6. A coronary sinus catheter assembly for the retrograde infusion of cardioplegia solution into the coronary sinus of a patient's heart, the catheter assembly comprising:

a catheter comprising:
   a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of cardioplegia solution to the catheter; and
   an inflatable balloon on the catheter tube generally adjacent the distal end of the catheter tube proximally of the infusion lumen outlet, the inflatable balloon having a plurality of outwardly-facing, spaced-apart, segmented, annular ribs or lands integrally molded with the balloon for engaging the coronary sinus, each segmented annular rib or land comprising a plurality of solid raised rib portions separated by non-raised portions extending annularly around the periphery of the balloon in alternating fashion, each raised rib portion having a non-conical upper surface sloping smoothly and gradually toward the surface of the balloon; and a stylet comprising:
   a handle; and
   a shaft extending from the handle and adapted to fit within the infusion lumen of the catheter, the shaft comprising:
      a generally elongate malleable wire having proximal and distal portions; and
      a generally elongate sleeve surrounding the proximal portion of the malleable wire, the sleeve being relative stiff in comparison with the malleable wire to provide stiffness to a proximal portion of the catheter;
      the distal portion of the malleable wire extending distally from the sleeve, the distal portion of the malleable wire being readily deformable in comparison with the sleeve, thereby facilitating deforming the malleable wire to hold the distal portion of the catheter in a desired configuration to facilitate the insertion of the catheter into the coronary sinus.

7. A coronary sinus catheter assembly according to claim 6 further comprising a plastic coating on the proximal portion of the malleable wire.

8. A coronary sinus catheter assembly according to claim 7 wherein the plastic coating is colored so that it is visible through the catheter.

9. A coronary sinus catheter assembly according to claim 8 wherein the malleable wire is an annealed stainless steel, the malleable wire having a Tenius-Olsen stiffness of between about 0.005 in/in and about 0.025 in/in.

10. A coronary sinus catheter assembly according to claim 9 wherein the deformable distal portion of the malleable wire has a length shorter than the length of the sleeve.

11. A coronary sinus catheter assembly according to claim 10 wherein the deformable distal portion of the malleable wire has a length of between about 1.5 and 6 inches, and the sleeve has a length of between 9 and 10 inches.

12. A coronary sinus catheter assembly according to claim 8 wherein the inflatable balloon is expandable from an un-inflated diameter, generally equal to the outer diameter of the catheter tube for introducing the catheter into the coronary sinus, to an inflated diameter, substantially greater than the outer diameter of the catheter tube for securing the distal end of the catheter in the coronary sinus.

13. A coronary sinus catheter assembly according to claim 12 wherein the non-raised portions preferentially stretch in comparison to the raised rib portions as the balloon is inflated to its inflated diameter.

14. A coronary sinus catheter assembly according to claim 13 wherein any two ribs or lands that are not separated from one another by a third rib or land constitute adjacent ribs or lands, and the raised rib portions of adjacent ribs or lands are staggered such that the raised rib portions of one rib or land are generally longitudinally aligned with the non-raised portions of the adjacent rib or land.

15. A coronary sinus catheter assembly according to claim 14 wherein the plurality of segmented ribs or lands comprises three to seven segmented ribs or lands.

16. A coronary sinus catheter assembly according to claim 14 wherein each segmented rib or land have the same number of raised rib portions and non-raised portions as the other ribs or lands.

17. A coronary sinus catheter assembly according to claim 6 wherein the malleable wire is an annealed stainless steel, the malleable wire having a Tenius-Olsen stiffness of between about 0.005 in/in and about 0.025 in/in.

18. A coronary sinus catheter assembly according to claim 6 wherein the deformable distal portion of the malleable wire has a length shorter than the length of the sleeve.

19. A coronary sinus catheter assembly according to claim 18 wherein the deformable distal portion of the malleable wire has a length of between about 1.5 and 6 inches, and the sleeve has a length of between 9 and 10 inches.

20. A coronary sinus catheter assembly according to claim 6 wherein the inflatable balloon is expandable from an un-inflated diameter, generally equal to the outer diameter of the catheter tube for introducing the catheter into the coronary sinus, to an inflated diameter, substantially greater than the outer diameter of the catheter tube for securing the distal end of the catheter in the coronary sinus.

21. A coronary sinus catheter assembly according to claim 20 wherein the non-raised portions preferentially stretch in comparison to the raised rib portions as the balloon is inflated to its inflated diameter.

22. A coronary sinus catheter assembly according to claim 6 wherein the non-raised portions preferentially stretch in comparison to the raised rib portions as the balloon is inflated to an inflated diameter.

23. A coronary sinus catheter assembly according to claim 6 wherein the plurality of segmented ribs or lands comprises three to seven segmented ribs or lands.

24. A coronary sinus catheter assembly according to claim 6 wherein each segmented rib or land has the same number of raised rib portions and non-raised portions as the other ribs or lands.

25. A coronary sinus catheter assembly according to claim 6 wherein the raised rib portions of adjacent ribs or lands are generally aligned along the longitudinal direction of the catheter.

26. A coronary sinus catheter assembly for the retrograde infusion of cardioplegia solution into the coronary sinus of a patient's heart, the catheter assembly comprising:

a catheter comprising:
  a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of cardioplegia solution to the catheter; and
  an inflatable balloon on the catheter tube generally adjacent the distal end of the catheter tube proximally of the infusion lumen outlet, the inflatable balloon being formed of elastomeric material and having a plurality of outwardly-facing, spaced-apart, segmented, annular ribs or lands integrally molded with the balloon for frictionally engaging the coronary sinus, each segmented annular rib or land comprising a plurality of solid raised rib portions separated by non-raised portions extending annularly around the periphery of the balloon in alternating fashion;
  the direction along the catheter tube from its proximal end toward its distal end constituting the forward direction, and the raised rib portions having a generally asymmetrical profile along the longitudinal direction of the catheter, the raised rib portions having an upper surface sloping smoothly and gradually forwardly to the surface of the balloon, and a back surface extending from the upper surface more steeply to the surface of the balloon than the upper surface slopes to the surface of the balloon; and
a stylet comprising:
  a handle; and
  a shaft extending from the handle and adapted to fit within the infusion lumen of the catheter, the shaft comprising:
    a generally elongate malleable wire having proximal and distal portions: and
    a generally elongate sleeve surrounding the proximal portion of the malleable wire, the sleeve being relative stiff in comparison with the malleable wire to provide stiffness to a proximal portion of the catheter;
    the distal portion of the malleable wire extending distally from the sleeve, the distal portion of the malleable wire being readily deformable in comparison with the sleeve, thereby facilitating deforming the malleable wire to hold the distal portion of the catheter in a desired configuration to facilitate the insertion of the catheter into the coronary sinus.

27. A coronary sinus catheter assembly according to claim 26 further comprising a plastic coating on the proximal portion of the malleable wire.

28. A coronary sinus catheter assembly according to claim 27 wherein the plastic coating is colored so that it is visible through the catheter.

29. A coronary sinus catheter assembly according to claim 28 wherein the malleable wire is an annealed stainless steel, the malleable wire having a Tenius-Olsen stiffness of between about 0.005 in/in and about 0.025 in/in.

30. A coronary sinus catheter assembly according to claim 29 wherein the deformable distal portion of the malleable wire has a length shorter than the length of the sleeve.

31. A coronary sinus catheter assembly according to claim 30 wherein the deformable distal portion of the malleable wire has a length of between about 1.5 and 6 inches, and the sleeve has a length of between 9 and 10 inches.

32. A coronary sinus catheter assembly according to claim 28 wherein the inflatable balloon is expandable from an un-inflated diameter, generally equal to the outer diameter of the catheter tube for introducing the catheter into the coronary sinus, to an inflated diameter, substantially greater than the outer diameter of the catheter tube for securing the distal end of the catheter in the coronary sinus.

33. A coronary sinus catheter assembly according to claim 32 wherein the non-raised portions preferentially stretch in comparison to the raised rib portions as the balloon is inflated to its inflated diameter.

34. A coronary sinus catheter assembly according to claim 33 wherein any two ribs or lands that are not separated from one another by a third rib or land constitute adjacent ribs or lands, and the raised rib portions of adjacent ribs or lands are staggered such that the raised rib portions of one rib or land are generally longitudinally aligned with the non-raised portions of the adjacent rib or land.

35. A coronary sinus catheter assembly according to claim 34 wherein the plurality of segmented ribs or lands comprises three to seven segmented ribs or lands.

36. A coronary sinus catheter assembly according to claim 34 wherein each segmented rib or land have the same number of raised rib portions and non-raised portions as the other ribs or lands.

37. A coronary sinus catheter assembly for the retrograde infusion of cardioplegia solution into the coronary sinus of a patient's heart, the catheter assembly comprising:
  a catheter comprising:
    a flexible, elongate catheter tube having proximal and distal ends and an outer diameter, and including at least an infusion lumen extending longitudinally through the tube and a lumen for pressure monitoring, at least one infusion lumen outlet generally adjacent the distal end of the catheter tube, and means adjacent the proximal end of the catheter tube for connecting a source of cardioplegia solution to the catheter, the direction longitudinally along the catheter from its proximal end toward its distal end constituting the forward direction; and
    an inflatable balloon on the catheter tube generally adjacent the distal end of the catheter tube proximally of the infusion lumen outlet, the inflatable balloon being formed of elastomeric material and having a plurality of outwardly-facing, spaced-apart, segmented, annular ribs or lands integrally molded with the balloon for frictionally engaging the coronary sinus, each segmented annular rib or land comprising a plurality of solid raised rib portions separated by non-raised portions extending annularly around the periphery of the balloon in alternating fashion, the inflatable balloon being expandable from an un-inflated diameter, generally equal to the outer diameter of the catheter tube for introducing the catheter into the coronary sinus, to an inflated diameter, substantially greater than the outer diameter of the catheter tube for securing the distal end of the catheter in the coronary sinus, the raised rib portions having a generally asymmetrical profile along the longitudinal direction of the catheter, the raised rib portions having an upper surface sloping smoothly and gradually forwardly to the surface of the balloon, and a back surface extending from the upper surface more steeply to the surface of the balloon than the upper surface slopes to the surface of the balloon; and
  a stylet comprising:

a handle; and a shaft extending from the handle and adapted to fit within the infusion lumen of the catheter, the shaft comprising:

a generally elongate malleable wire having proximal and distal portions; and a generally elongate sleeve surrounding the proximal portion, of the malleable wire, the sleeve being relative stiff in comparison with the malleable wire to provide stiffness to a proximal portion of the catheter;

the distal portion of the malleable wire extending distally from the sleeve, the distal portion of the malleable wire being readily deformable in comparison with the sleeve, thereby facilitating deforming the malleable wire to hold the distal portion of the catheter in a desired configuration to facilitate the insertion of the catheter into the coronary sinus.

38. A coronary sinus catheter assembly according to claim 37 wherein the non-raised portions preferentially stretch in comparison, to the raised rib portions as the balloon is inflated to its inflated diameter.

39. A coronary sinus catheter assembly according to claim 38 wherein any two ribs or lands that are not separated from one another by a third rib or land constitute adjacent ribs or lands, and the raised rib portions of adjacent ribs or lands are staggered such that the raised rib portions of one rib or land are generally longitudinally aligned with the non-raised portions of the adjacent rib or land.

40. A coronary sinus catheter assembly according to claim 39 wherein the plurality of segmented ribs or lands comprises three to seven segmented ribs or lands.

41. A coronary sinus catheter assembly according to claim 40 wherein each segmented rib or land has the same number of raised rib portions and non-raised portions as the other ribs or lands.

42. A coronary sinus catheter assembly according to claim 37 wherein the raised rib portions of adjacent ribs or lands are staggered such that the raised rib portions of one rib or land are generally longitudinally aligned with the non-raised portions of the adjacent rib or land.

43. A coronary sinus catheter assembly according to claim 42 wherein the plurality of segmented ribs or lands comprises three to seven segmented ribs or lands.

44. A coronary sinus catheter assembly according to claim 43 wherein each segmented rib or land having the same number of raised rib portions and non-raised portions as the other ribs or lands.

45. A coronary sinus catheter assembly according to claim 37 wherein the plurality of segmented ribs or lands comprises three to seven segmented ribs or lands.

* * * * *